US00PP37665P3

(12) United States Plant Patent
Skotak, Jr.

(10) Patent No.: US PP37,665 P3
(45) Date of Patent: Sep. 1, 2026

(54) *AECHMEA* PLANT NAMED 'A2508'

(50) Latin Name: *Aechmea fasciata.*
Varietal Denomination: A2508

(71) Applicant: Chester Skotak, Jr., Alajuela (CR)

(72) Inventor: Chester Skotak, Jr., Alajuela (CR)

( * ) Notice: Subject to any disclaimer, the term of this patent is extended or adjusted under 35 U.S.C. 154(b) by 0 days.

(21) Appl. No.: 19/393,349

(22) Filed: Nov. 18, 2025

(65) Prior Publication Data

US 2026/0157246 P1 Jun. 4, 2026

(30) Foreign Application Priority Data

Nov. 29, 2024 (QZ) ..... PBR 2024/2862

(51) Int. Cl.
*A01H 5/02* (2018.01)
*A01H 5/12* (2018.01)
*A01H 6/22* (2018.01)

(52) U.S. Cl.
USPC ..... Plt./370
CPC ..... *A01H 6/22* (2018.05); *A01H 5/02* (2013.01); *A01H 5/12* (2013.01)

(58) Field of Classification Search
USPC ..... Plt./370
CPC ... A01H 5/02; A01H 5/12; A01H 5/00; A01H 6/22
See application file for complete search history.

(56) References Cited

U.S. PATENT DOCUMENTS

PP12,685 P2 * 6/2002 Bak ..... A01H 5/02
Plt./370

OTHER PUBLICATIONS

Botany Brisbane *Aechmea fasciata* retrieved on Mar. 16, 2026 at https://www.botanybrisbane.com/plants/bromeliaceae/aechmea/aechmea-fasciata/, 13 pp. (Year: 2026).*
CPVO Application Consultation Version 4.25.11, retrieved on Mar. 12, 2026 at https://online.plantvarieties.eu/publicConsultationDetails?registerId=20242862&denomination=a2508, 2 pp. (Year: 2026).*

* cited by examiner

*Primary Examiner* — June Hwu
(74) *Attorney, Agent, or Firm* — James R. Holm; Plant Novelty Rights, LLC

(57) ABSTRACT

A new and distinct *Aechmea* plant named 'A2508' particularly distinguished by a compact plant habit with a flattened, obovate rosette form; variegated foliage with green to greyed-green background and irregular silver transverse banding; an absence of spines on the leaf margins; inflorescence positioned slightly above the foliar plane with bright pink floral bracts and violet-blue flowers; moderate vigor and high uniformity in tissue culture propagation; and a production time of approximately 26 months from a tissue cultured plantlet to a saleable flowering plant under commercial greenhouse conditions in Evergem, Belgium.

3 Drawing Sheets

Figure 1:
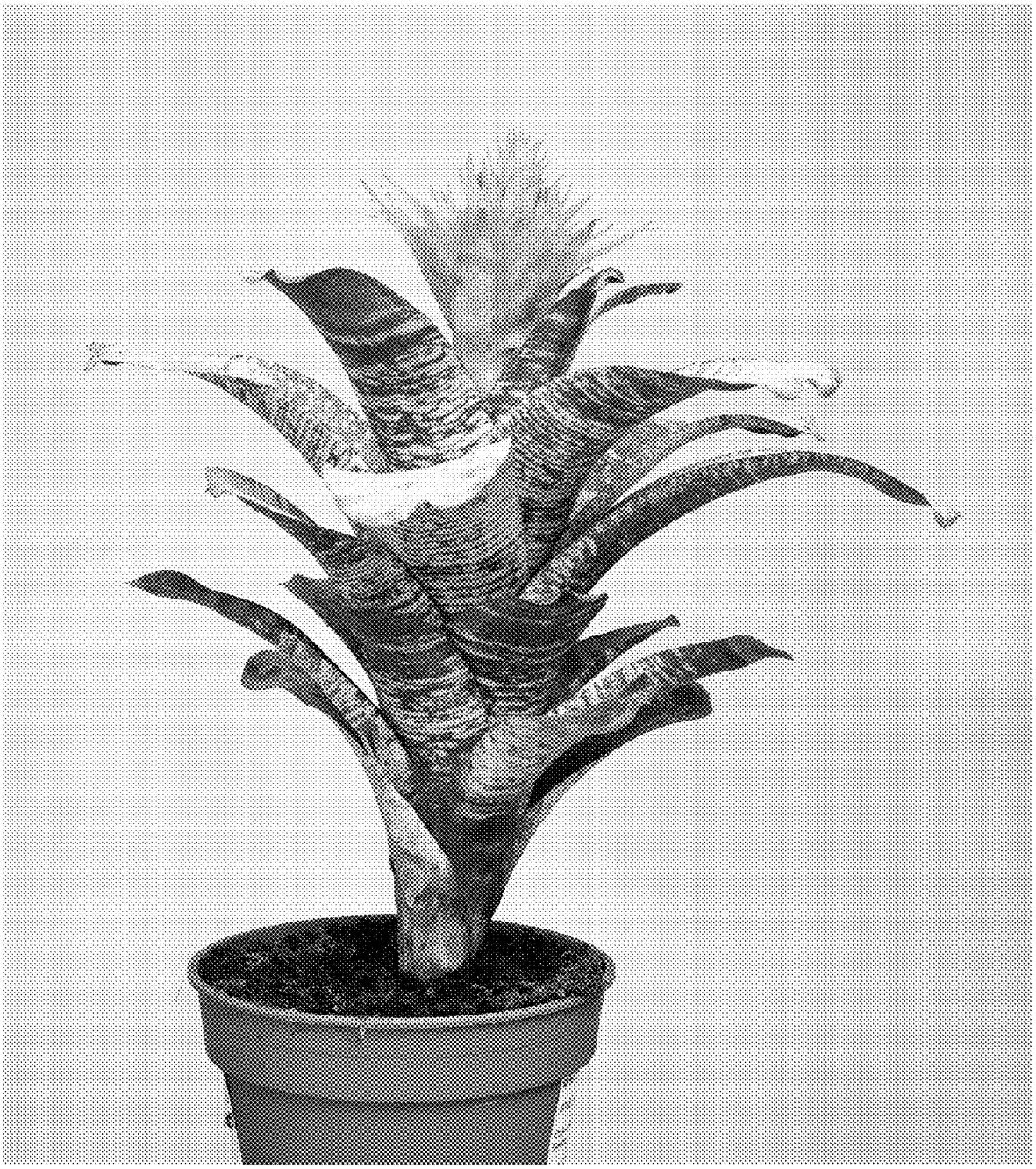

Genus and species: *Aechmea fasciata.*
Variety denomination: 'A2508'.

STATEMENT REGARDING PRIOR DISCLOSURES BY THE INVENTOR

This application claims priority to CPVO application no. 2024/2862 filed on Nov. 29, 2024, which is herein incorporated by reference. The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the filing date.

BACKGROUND OF THE NEW PLANT

The present invention comprises a new and distinct variety of *Aechmea* plant, botanically known as *Aechmea fasciata*, and hereinafter referred to by the variety name 'A2508'.

*Aechmea* comprises a genus of more than 168 species of evergreen perennials suitable for cultivation in the home or in the greenhouse. *Aechmea* may be terrestrial or epiphytic. For the most part, the species vary in diameter from 12 to 18 inches to 3 or 4 feet and have rosettes of spiny-edged leaves.

Flowers and bracts of *Aechmea* frequently have brilliant colors and may last for several months. The range of colors for *Aechmea* is generally from the yellow through orange but may also include pink, orange, red and red-purple. Tubular, three-petalled flowers may also appear but are usually short-lived.

*Aechmea* may be grown as pot plants for greenhouse or home use. Typically, the plants are shaded from direct sunlight; and the central, vaselike part of the leaf rosette is normally filled with water.

*Aechmea* is native to tropical America. Leaves of *Aechmea* are usually formed from basal rosettes which are entire and in several vertical ranks. *Aechmea* has terminal spikes or panicles which are often bracted with petals united in a tube longer than the calyx.

Asexual propagation of *Aechmea* is frequently done through meristematic tissue culture. Propagation can also be from offshoots which can be detached from the mother plant and grown in an appropriate soil or bark mixture. Methods for cultivating and crossing of *Aechmea* are well known.

The new *Aechmea* variety 'A2508' is the product of a controlled cross pollination conducted by the inventor in Alajuela, Costa Rica in May 2012. The objective of the breeding program was to develop compact *Aechmea fasciata* plants suitable for pot production, characterized by uniform foliage, reduced spines, and improved floral presentation. The female or seed parent was an unnamed and unpatented *Aechmea fasciata* breeding line. The male or pollen parent was an unnamed and unpatented *Aechmea fasciata* breeding line. 'A2508' was selected by the inventor in June 2019 in Alajuela, Costa Rica as a single flowering plant from within the progeny of the stated cross.

The new *Aechmea* cultivar 'A2508' was first reproduced asexually by meristematic tissue culture in January 2018 at a commercial laboratory in Evergem, Belgium. Asexual propagation by meristematic tissue culture of the new variety has shown that the unique features of the new variety are stable and reproduced true-to-type to date through 6 successive generations.

SUMMARY OF THE INVENTION

The new *Aechmea* cultivar 'A2508' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Aechmea* cultivar. The combination of these characteristics distinguishes 'A2508' as a new and distinct variety of *Aechmea*.

1. *Aechmea* 'A2508' exhibits a compact plant habit with a flattened, obovate rosette form.
2. *Aechmea* 'A2508' exhibits variegated foliage with green to greyed-green background and irregular silver transverse banding.
3. *Aechmea* 'A2508' exhibits an absence of spines on the leaf margins.
4. *Aechmea* 'A2508' exhibits inflorescence positioned slightly above the foliar plane with bright pink floral bracts and violet-blue flowers.
5. *Aechmea* 'A2508' exhibits moderate vigor and high uniformity in tissue culture propagation.
6. *Aechmea* 'A2508' exhibits a production time of approximately 26 months from a tissue cultured plantlet to a saleable flowering plant under commercial greenhouse conditions in the Evergem, Belgium.

DESCRIPTION OF THE PHOTOGRAPHS

This new *Aechmea* cultivar is illustrated by the accompanying-colored photographs which show the overall appearance and distinct characteristics of the plant. The colors shown are as true as can be reasonably obtained by conventional photographic procedures. The photographs are of 26-month-old plants grown in 17-centimeter circular containers in a conventional glass greenhouse in Evergem, Belgium. Colors in the photographs may differ slightly from the color values cited in the botanical description which accurately describes the colors of the new variety.

FIG. 1. shows the overall plant form, foliage, and inflorescence of 'A2508'.

Figure 2:
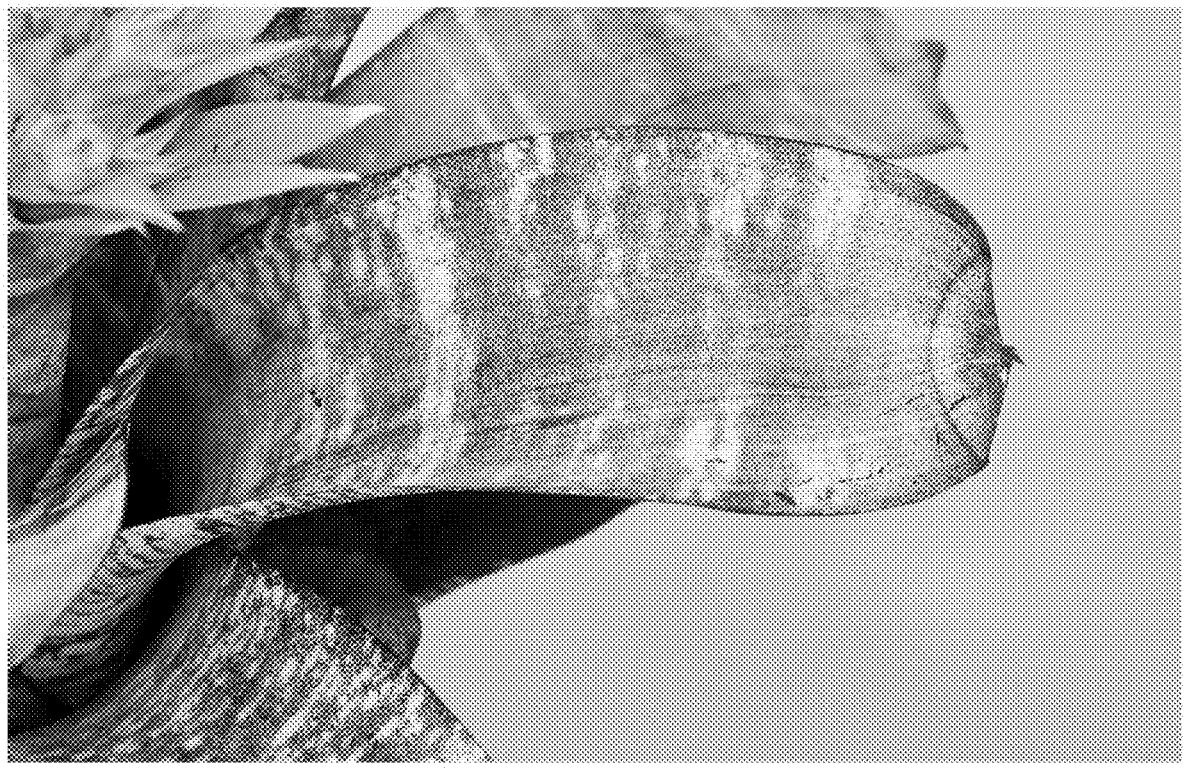

FIG. 2. shows a close-up of a typical mature leaf of 'A2508'.

Figure 3:
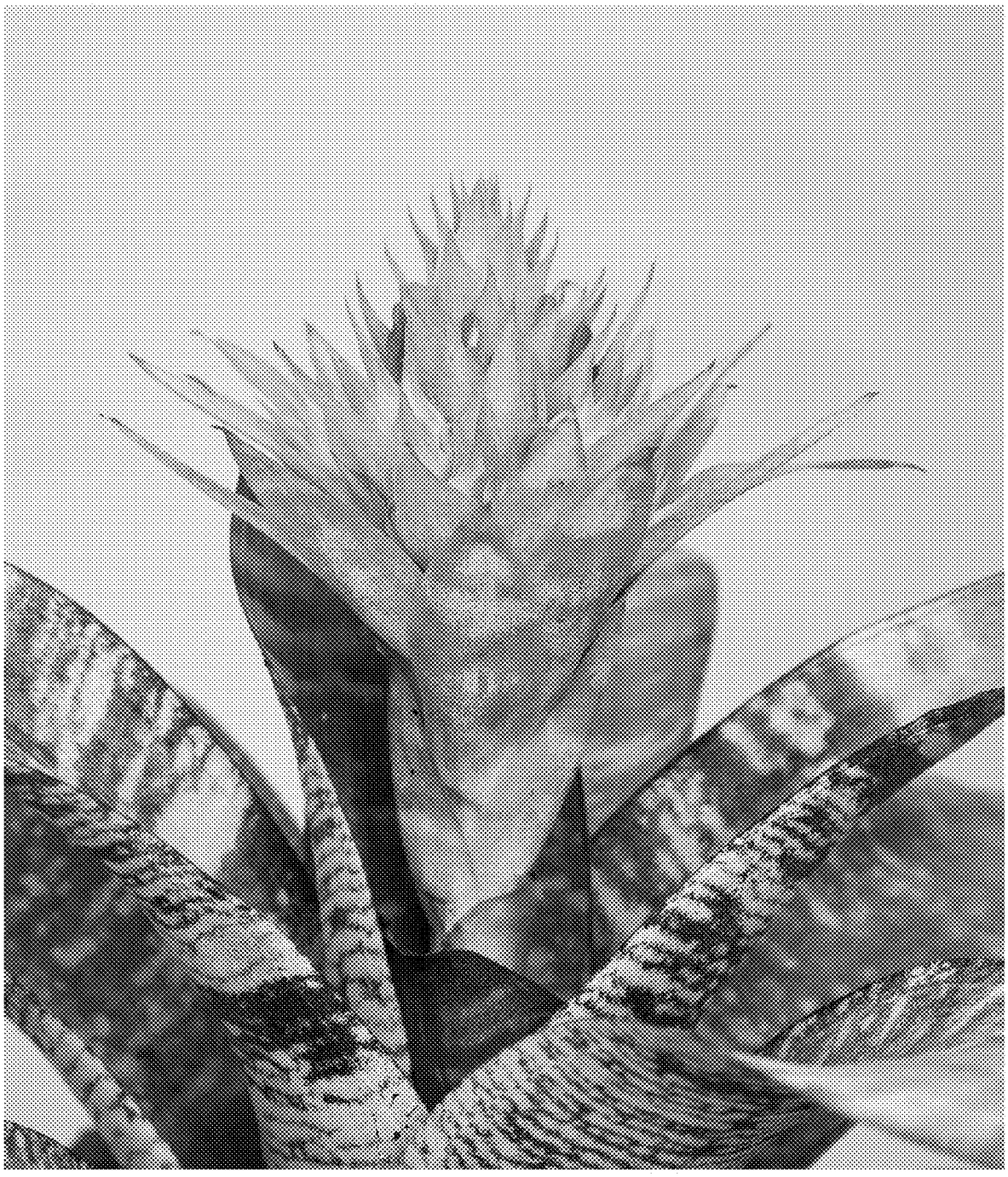

FIG. 3. shows a close-up of typical inflorescence of 'A2508'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in a commercial greenhouse located in Evergem, Belgium. Plants were grown under maximum light levels of approximately 12,000 lux. Detailed descriptions were taken in November 2024 from 26-month-old plants grown in 17-centimeter circular containers. Measurements and numerical values represent averages of typical plant types.

DETAILED BOTANICAL DESCRIPTION

Classification:

*Family*.—Bromeliaceae.

*Botanical*.—*Aechmea fasciata*.

*Denomination*.—'A2508'.

General description:

*Plant type*.—Tropical perennial suitable as an indoor potted plant.

*Growth habit*.—Basal rosette, inflorescence grows from the center of the basal rosette.

*Overall plant shape*.—Flattened obovate with inflorescence carried slightly above the foliar plane.

*Height from soil level to top of foliar plane*.—28.3 cm.

*Height from soil level to top of floral plane*.—33.0 cm.

*Plant diameter or area of spread*.—32.8 cm.

*Growth rate*.—Moderate.

*Plant vigor*.—Moderate.

*Branching habit*.—No lateral branching; leaves in a basal rosette, inflorescence grows from the center of the basal rosette.

*Propagation type*.—Meristematic tissue culture.

*Time to produce a finished plant*.—Approximately 26 months from a tissue cultured plantlet.

Root description:

*General*.—Slightly fleshy and very slightly fibrous.

*Length*.—Average 5.4 cm.

*Width*.—Average 0.1 cm.

*Color*.—165B (greyed-orange).

Foliage description:

*Arrangement*.—Rosulate.

*Division*.—Simple.

*Quantity of leaves per rosette*.—23.

*Lamina*.—Shape: Oblong. Length: Average 22.0 cm. Width: Average 7.1 cm. Aspect: Moderately concave, curled downward, leaf tips are near horizontal. Apex shape: Truncate to broadly retuse with a mucronulate tip. Base: Sheathing. Sheath length: 5.0 cm. Sheath width 8.9 cm. Sheath color: N186C (greyed-purple), fading to 146A (yellow-green) in the center and fading to 146C and 146D (yellow-green) at the margins. Margin: Entire. Undulation: No undulation. Lobes: Unlobed. Texture (both upper and lower surfaces): Smooth, glabrous. Rugosity: Non-rugose. Pubescence: Not present. Luster: Upper surface: Slightly glossy. Lower surface: Matte.

Color: Juvenile foliage: Upper surface: 191C (greyed-green), slightly blotched darker 191A, and lighter 192B and 192C; blotches are loosely arranged in radial lines across the lamina. Lower surface: 146D (yellow-green), slightly blotched 192C (greyed-green); blotches are loosely arranged in radial lines across the lamina. Mature foliage: Upper surface: A blend of 139A (green) and N189A (greyed-green), covered by a thin waxy layer of 202C (black) and blotched with 192C (greyed-green); blotches are loosely arranged in radial lines across the lamina. Lower surface: 147A (yellow-green) and blotched N155A (white); blotches are loosely arranged in radial lines across the lamina with the upper one-fifth of the lamina unblotched. Venation: Pattern: Parallel. Color (mature foliage): Upper surface: Upper surface venation is colored the same as the upper surface of the lamina. Lower surface: Lower surface venation is colored the same as the lower surface of the lamina.

Inflorescence description:

*Arrangement*.—Terminal panicle.

*Type and form*.—Panicle, consisting of a main panicle and an average of 11 secondary panicles, each consisting of an average of 10 individual flowers.

*Height*.—Average 8.1 cm, excluding peduncle.

*Diameter*.—Average 12.6 cm.

*Quantity of flowers per inflorescence*.—Average 30.

*Quantity of flowers and flower buds per plant*.—Average 150.

*Natural flowering season*.—Continuously.

*Time to flower or response time*.—6 months.

*Flower bud*.—Length: Average 1.3 cm. Diameter: 0.6 cm. Shape: Elliptic-oblong. Texture: Smooth and glabrous. Luster: Very slightly glossy. Color: 97A (violet-blue) with a blend of 79A (purple) and 97B (purplish blue), lower three-quarters of bud colored 155C (white) and tinged 75C (purple).

*Flower*.—Type and form: Single, rotate. Aspect: Upright and outwardly. Habit: Freely. Fragrance: Not fragrant. Shape: Rotate, petals not opening but remaining in oblanceolate shape. Vertical height: Average 0.6 cm. Horizontal diameter: Average 0.6 cm. Length (depth): Average 2.6 cm. Tube texture (both sides): Smooth and glabrous. Longevity: Average 4 weeks. Persistence: Persistent.

*Petals*.—Arrangement: Rotate. Quantity per flower: Average 3. Number of petal whorls: Average 1. Petal fusion: Not fused. Length: Average 2.3 cm. Width: Average 0.4 cm. Shape: Narrow oblong, concave. Tip: Obtuse. Base: Cuneate. Margin: Entire. Margin undulation: Not undulated. Texture (both upper and lower surfaces): Smooth and glabrous. Rugosity (both upper and lower surfaces): Non-rugose. Luster (both upper and lower surfaces): Slightly glossy. Color when opening and fully opened: Upper surface: 68B (red-purple), fading to a transparent NN155D (white) towards the base. Lower surface: 68A (red-purple), fading to a transparent NN155D (white) towards the base. Color when fading (both upper and lower surfaces): Not fading. Venation: Inconspicuous. Petaloids: Not present.

*Calyx*.—Shape: Rotate. Length: Average 1.4 cm. Diameter: 0.6 cm.

*Sepals*.—Arrangement: Rotate. Quantity per flower: Average 3. Quantity of sepal whorls: 1. Length: Average 1.3 cm. Width: Average 0.5 cm. Sepal fusion: Not fused. Shape: Oblong, strongly concave. Apex or tip: Broadly acute. Base: Cuneate. Margin: Entire. Texture (both upper and lower surfaces): Glabrous and smooth. Luster (both upper and lower surfaces): Slightly glossy. Color when opening and fully opened: Upper surface: Transparent N155A (white) with a small blotch of 73D (red-purple) near the top. Lower surface: Transparent N155A (white) with a small blotch of 73C to 73D (red-purple) near the top. Sepal spurs: Not present.

*Peduncle*.—Terminal length: Average 28.2 cm. Terminal diameter: Average 1.2 cm. Angle: Vertical. Strength: Strong. Texture: Covered with a felt colored 155C (white). Luster: Slightly glossy but covered with a matte felt. Color: 144B (yellow-green).

*Pedicels*.—Not Present, individual flowers sessile.

*Scape bracts*.—General description: Scape bracts are present at the base of the inflorescence and on the scape (peduncle). Shape: Lanceolate. Length: Average 9.0 cm. Width: Average 2.0 cm. Apex: Acute, with a mucronate tip. Color (outer, visible surface): 62A (red-purple), fading lighter towards the base, 62B and 62C (red-purple), tipped 194B (greyed-green) and banded 69D (red-purple) with strong greenish infusions of 193A (greyed-green), especially on the lower scape bracts.

*Primary bracts*.—General description: Fertile bracts are present at the top of the peduncle of the main panicle and at the base of each secondary panicle. Shape: Lanceolate. Length: Average 7.55 cm. Width: Average 2.3 cm. Luster (both sides): Slightly glossy. Margin: Entire. Apex: Acute, with a mucronate tip. Base: Broadly cuneate. Color: Upper surface: 65A (red-purple), fading lighter towards the base, 65B (red-purple), and tipped 192A (greyed-green). Lower surface: 62A (red-purple), fading lighter towards the base, 62B and 62C (red-purple) and tipped 194B (greyed-green).

*Floral bracts*.—(Below each spike of individual flowers). General description: Below each spike of individual flowers, a single bract is present. Shape: Ovate and concave. Length: Average 3.7 cm. Width: Average 1.3 cm. Luster (both sides): Slightly glossy. Margin: Finely serrate to entire. Apex: Long apiculate with a pungent, sharp tip. Base: cuneate. Sheath color: Upper surface: 62B (red-purple), fading to 157C (green-white) at the base. Lower surface: 62B (red-purple), fading to 155C (white) at the base.

*Reproductive organs*.—Quantity of stamens per flower: 6. Filament: Length: Average 1.7 cm. Color: NN155D (white). Anther: Shape: Dorsifixed, narrow elliptic. Length: Average 0.5 cm. Width: Average 0.1 cm. Color: 155B (white). Pollen amount: None observed. Pistil: Quantity: 1. Length: Average 2.2 cm. Stigma: Shape: Cleft; three-parted, stigmas fringed. Length: Average 0.2 cm. Diameter: Average 0.1 cm. Color: 155C (white). Style: Length: Average 2.0 cm. Color: NN155C (white). Ovary color: 155B (white).

Fruit and seed set: None observed to date.

Temperature tolerances: USDA Zones 10 to 13; at least tolerant of temperatures to 40 degrees Celsius.

Rain tolerance: High.
Wind tolerance: High.
Disease and pest tolerance: No claims are made to any superior disease or insect resistance or tolerance.

COMPARISON WITH THE PARENT PLANTS

The new *Aechmea* cultivar 'A2508' can be distinguished from its female or seed parent in the following characteristics described in Table 1 below.

TABLE 1

| Characteristic | 'A2508' | Female parent |
|---|---|---|
| Overall plant size | More compact, flattened rosette | Larger, more open rosette |
| Leaf margin | Spineless | Spined |
| Leaf variegation | Strong silver banding | Weak, less silver banding |
| Leaf color (upper surface) | Green to greyed-green silver pattern | Dark green-grey |
| Inflorescence size | Compact and proportionate | Larger, more elongated |
| Primary bract color | Bright pink (65A and 65B) | Pale pink |
| Flowering position | Slightly above foliar plane | Partly within the rosette |

The new *Aechmea* cultivar 'A2508' can be distinguished from its male or pollen parent in the following characteristics described in Table 2 below.

TABLE 2

| Characteristic | 'A2508' | Male Parent |
|---|---|---|
| Overall plant size | Compact and even rosette | Taller than 'A2508', less symmetrical |
| Leaf margin | Spinless | Small spines present |
| Leaf width | Wider than male parent | Narrower than 'A2508' |

TABLE 2-continued

| Characteristic | 'A2508' | Male Parent |
|---|---|---|
| Leaf variegation | Strong and consistent | Moderate, uneven |
| Inflorescence color | Deeper pink | Lighter pink |
| Inflorescence form | Fuller and denser | Slenderer |
| Flower color | Red-purple with violet-blue buds | Light pink with faint blue |

COMPARISON WITH RELATED KNOWN VARIETY

The new *Aechmea* cultivar 'A2508' can be distinguished from the related known variety of *Aechmea* 'Primera' (U.S. Plant Pat. No. 12,685) in the following characteristics described in Table 3 below.

TABLE 3

| Characteristic | 'A2508' | 'Primera' |
|---|---|---|
| Plant habit | Lower and wider rosette | Taller and more upright |
| Leaf size | Shorter and broader leaves | Longer and narrower leaves |
| Leaf coloration | Irregular, blotchy silver markings | Strong horizontal silver banding |
| Leaf aspect | Outward and downward | Upward and inward |
| Inflorescence position | Compact and rounded, held just above foliage | Taller and more elongated, held higher above foliage |
| Bract color | Uniformly red-purple | Lighter and more translucent |

What is claimed is:

1. A new and distinct cultivar of *Aechmea* plant named 'A2508', substantially as illustrated and described herein.

* * * * *